United States Patent [19]

Ueno et al.

[11] 4,210,640

[45] Jul. 1, 1980

[54] SUBLIMABLE FUNGICIDAL COMPOSITIONS CONTAINING TRIISOPROPYL- OR TRITERTIARY-BUTYL-S-TRIOXANE CARRIERS

[75] Inventors: Yasuhiko Ueno, Kawanishi; Yoshito Saeki, Suita; Takuya Akiyama, Nagaokakyo; Masao Fujita, Amagasaki, all of Japan

[73] Assignee: Ogawa & Co., Ltd., Osaka, Japan

[21] Appl. No.: 931,444

[22] Filed: Aug. 7, 1978

Related U.S. Application Data

[60] Division of Ser. No. 737,196, Oct. 29, 1976, Pat. No. 4,123,525, which is a continuation-in-part of Ser. No. 463,176, Apr. 22, 1974, abandoned.

[30] Foreign Application Priority Data

Jun. 15, 1973 [JP] Japan ................................. 48-68013
Jun. 15, 1973 [JP] Japan ................................. 48-68014

[51] Int. Cl.$^2$ .................... A01N 9/00; A01N 9/28; A01N 9/36
[52] U.S. Cl. .................... 424/181; 424/44; 424/225; 424/244; 424/283
[58] Field of Search ............... 424/225, 244, 283, 181

[56] References Cited

FOREIGN PATENT DOCUMENTS

| 46-21232 | 6/1971 | Japan | 424/283 |
| 47-24731 | 7/1972 | Japan | 424/225 |
| 48-3379 | 1/1973 | Japan | 424/283 |
| 49-69834 | 5/1974 | Japan | 424/225 |

OTHER PUBLICATIONS

CIBA Ltd., "Prep. of Materials for Protracted, Etc.," (1964), CA 62, p. 9720 (1965).
Paulet et al., "Prep. and Polymerization of Etc.," (1966), CA 65, p. 9034 (1966).
Chretien-Bessiere et al., "4-Methyl-2-Pentenal, Etc.," (1962), CA 57, p. 13636 (1962).
Vekhnovskaya et al., "The Action of Activated Clay, Etc.," (1962), CA 59, pp. 429-430 (1963).

*Primary Examiner*—Glennon H. Hollrah
*Attorney, Agent, or Firm*—Wenderoth, Lind & Ponack

[57] ABSTRACT

An improvement is provided in sublimable agricultural chemical compositions in the form of rough grains, pulverized powders or tablets which comprises at least one agricultural chemical and a carrier therefor. The improvement resides in the employment as the carrier, triisopropyl-s-trioxane or tritertiary-butyl-s-trioxane.

8 Claims, No Drawings

SUBLIMABLE FUNGICIDAL COMPOSITIONS CONTAINING TRIISOPROPYL- OR TRITERTIARY-BUTYL-S-TRIOXANE CARRIERS

CROSS REFERENCE TO RELATED APPLICATION

This is a division of application Ser. No. 737,196, filed Oct. 29, 1976, now U.S. Pat. No. 4,123,525, which in turn is a continuation-in-part of application Ser. No. 463,176, filed Apr. 22, 1974, the latter application being now abandoned.

BACKGROUND OF THE INVENTION

I. Field of the Invention

The present invention relates to sublimable agricultural chemical compositions in the form of rough granules, pulverized powders or tablets comprising triisopropyl-s-trioxane (hereinafter referred to as trioxane (1)) or tritertiarybutyl-s-trioxane (hereinafter referred to as trioxane (2)) as a diluent or carrier and one or more agricultural chemical mixed therewith. In the above, the term agricultural chemicals means insecticides, fungicides, rodenticides, herbicides, supplemental agents and the like, and the term sublimable agricultural compositions includes a broader range of materials such as insecticides for environmental sanitation, especially for domestic use.

II. Description of the Prior Art

Conventionally, agricultural chemical compositions including fungicides, insecticides, rodenticides, herbicides, supplemental agents or the like have been used in the form of wettable powders, emulsions, powders, granules, aerosols and the like. Among them, those in the form of powder and grain each comprise a carrier or a diluent in a powdery state such as sulfur, silicon, talc, diatomaceous earth, silica, calcium hydroxide, apatite, calcite, dolomite, gypsum, mica, pyrophyllite, clay, pumice and the like and one of the agricultural chemicals mixed therein.

SUMMARY OF THE INVENTION

A main object of the present invention is to provide diluents or carriers superior in properties to conventional ones as above-mentioned.

Most of the conventional diluents or carriers used in solid agricultural compositions were inorganic substances or compounds and agricultural chemicals merely attached to their surface or were mixed therewith. Such conventional carriers were also unable to prevent the decomposition of agricultural chemicals and remained in the soil after used without subliming.

In contrast, when either mixed directly with an agricultural chemical or mixed therewith after melting, the two trioxanes of the present invention produce agricultural chemical compositions in which the agricultural chemical is contained in a crystalline trioxane. Therefore, the chemical hardly decomposes or changes in nature. When the composition is used on the soil, both of the trioxanes of the present invention gradually sublime with the result that the chemicals remain effective for a long period of time. Neither trioxane remains in the soil. The sublimable agricultural chemical compositions of the present invention may be sprinkled in the air, on the soil, or in a paddy field.

Trioxane (1) or (2) used as a diluent or carrier for manufacturing the sublimable agricultural chemical compositions in the present invention are characterized by the following advantages over conventional carriers or diluents.

Trioxane (1), produced by cyclizing and trimerizing isobutylaldehyde with mineral acid, halogen, zinc chloride, phosphorous pentoxide and the like, is a pure white crystal showing vapor pressures of 0.31 mmHg at 20° C. and 0.95 mmHg at 30° C. with its melting point at 62.5° C. Another pure white crystal trioxane (2), also compounded by cyclizing and trimerizing trimethylacetaldehyde in the same method as above, shows vapor pressure of 0.12 mmHg at 20° C. and 0.38 mmHg at 30° C. and has a melting point of 92.0° C.

Both of the trioxanes are chemically stable, water-insoluble, and lighter in specific gravity than water which enables them to float on the surface of water, such property being advantageous for their adhesion to partially submerging plants such as paddy (rice) and the like. These two trioxanes are tasteless and odorless and are able to maintain their form in the form of rough grain or pulverized powder even if they contain oil up to 20%, said property being advantageous for scattering. The materials are also moderately sublimable, which means they do not accumulate within the soil. Sublimable agricultural compositions in the form of rough grains or pulverized powders produced by mixing either trioxane with one or more agricultural chemicals are such that they attach to watery agricultural plants without undesirably scattering over a wide territory, wherein the compositions remain effective over a long period of time due to the moderate sublimability of the carriers. The compositions also produce the same effect when scattered on the soil.

The trioxanes of the present invention are nontoxic to men and domestic animals and harmless to plants. We attempted to determine the $LD_{50d}$ or median lethal dose of trioxane (1) by use of rats and mice, but these attempts were in vain. Even as large a dose as 10,000 mg per kilogram of body weight caused no death. Also, trioxane (1) did not show either chronic or inhalation toxicity, nor did this material produce any toxic substances with activated sludges. This shows that said trioxane is very stable and is in no way toxic. Trioxane (2) presumably has similar properties to trioxane (1) in this regard.

As described before, either trioxane (1) or (2) can be mixed with an insecticide so as to volatilize the insect-killing vapor for a long period of time, which means that the product is desirable on a commercial scale for environmental sanitation, especially for domestic use.

DESCRIPTION OF THE PREFERRED EMBODIMENTS

The following examples serve to illustrate the preferred method for preparing the compositions of the present invention, the examples imposing no limitation on the scope of claims in the present invention. (Hereinafter, "parts" denotes "weight parts".)

EXAMPLES (Examples 1–16 cover insecticides, 17–20 fungicides, and 21–27 herbicides.)

1. 970 parts of trioxane (1) was mixed evenly with 30 parts of S-(1,2-dicarbethoxyethyl)-O,O-dimethyldithiophosphate (hereinafter called malathion), to produce an insecticidal composition in the form of rough powders for control of insects in a paddy field.

2. 980 parts of trioxane (1) was mixed thoroughly with 20 parts of dimethyl-2,2-dichlorovinyl phosphate (hereinafter called DDVP) to produce an insecticidal composition in the form of rough powders for control of *Musca domestica* and insects on mulberry and tea trees.

3. 950 parts of trioxane (1) was mixed evenly with 50 parts of O,O-diethyl-O-(2-isopropyl-4-methylpyrimidyl(6))-thiophosphate (hereinafter called Diazinon) to produce an insecticidal composition in the form of rough powders for control of insects on paddy, fruit trees and vegetables.

4. 970 parts of trioxane (1) was mixed thoroughly with 30 parts of O,O-dimethyl-O-(3-methyl-4-nitrophenyl)thiosphophate to produce an insecticidal composition in the form of rough powders for control of insects on paddy, fruit trees and vegetables.

5. 930 parts of trioxane (1) was mixed evenly with 70 parts of ethyl-O,O-dimethyldithiophosphorylphenylacetate to produce an insecticidal composition in the form of rough powders for control of insects on paddy, fruit trees and vegetables.

6. 990 parts of trioxane (1) was mixed evenly with 10 parts of O,O-dimethyl-1-hydroxy-2,2,2-trichloroethylphosphate to produce an insecticidal composition in the form of rough powders for control of the flies, mosquitoes and cockroaches.

7. 950 parts of trioxane (1) was mixed evenly with 50 parts of O,O-dimethyl-O-(3-methyl-4-methylthiophenyl) thiophosphate to produce an insecticidal composition in the form of rough powders for control of insects on paddy, fruit trees and vegetables.

8. 930 parts of trioxane (1) was mixed evenly with 70 parts of O,O-dimethyl-S-phthalimido-methyl dithiophosphate to produce an insecticidal composition in the form of rough powders for control of insects on cotton.

9. 985 parts of trioxane (1) was mixed thoroughly with 15 parts of ethyl-O-p-nitrophenyl phenylphosphonothioate to produce an insecticidal composition in the form of rough powders for control of insects on paddy, fruit trees and vegetables.

10. 980 parts of trioxane (2) was mixed evenly with 20 parts of 2-sec.-butylphenyl-N-methylcarbamate to produce an insecticidal composition in the form of rough powders for control of insects on paddy, fruit trees and vegetables.

11. 950 parts of trioxane (2) was mixed evenly with 50 parts of 1-naphthyl-N-methylcarbamate to produce an insecticidal composition in the form of rough powders for control of insects on paddy, fruit trees and vegetables.

12. 990 parts of trioxane (2) was mixed evenly with 10 parts of 2-isopropoxyphenyl-N-methylcarbamate to produce an insecticidal composition in the form of rough powders for control of insects on paddy, fruit trees and vegetables.

13. 980 parts of trioxane (2) was mixed evenly with 20 parts of 2-isopropylphenyl-N-methylcarbamate to produce an insecticidal composition in the form of rough powders for control of insects on paddy, fruit trees and vegetables.

14. 980 parts of trioxane (2) was mixed evenly with 20 parts of 3,4-xylyl-N-methylcarbamate to produce an insecticidal composition in the form of rough powders for control of insects on paddy, fruit trees and vegetables.

15. 970 parts of trioxane (2) was mixed evenly with 30 parts of m-tolyl-N-methylcarbamate to produce an insecticidal composition in the form of rough powders for control of insects on paddy, fruit trees and vegetables.

16. 980 parts of trioxane (2) was mixed evenly with 20 parts of 3,5-xylyl-N-methylcarbamate to produce an insecticidal composition in the form of rough powders for control of insects on paddy, fruit trees and vegetables.

17. 830 parts of trioxane (1) was mixed evenly with 170 parts of O,O-diisopropyl-S-benzylthiophosphate to produce a fungicidal composition in the form of pulverized powders for killing fungus on paddy, etc.

18. 975 parts of trioxane (1) was mixed evenly with 25 parts of O-ethyl-S,S-diphenyldithiophosphate (hereinafter called EDDP) to produce a fungicidal composition in the form of pulverized powders for killing fungus on paddy, etc.

19. 970 parts of trioxane (2) was mixed evenly with 30 parts of O-butyl-S-ethyl-S-benzyl-phosphorodithioate to produce a fungicidal composition in the form of pulverized powders for killing fungus on paddy, etc.

20. 996.6 parts of trioxane (2) was mixed evenly with 3.4 parts of the hydrochloric salt of Kasugamycin to produce a fungicidal composition in the form of pulverized powders for killing fungus on paddy, etc.

21. 910 parts of trioxane (1) was mixed evenly with 90 parts of 2,4,6-trichlorophenyl-4'-nitrophenyl ether to produce a herbicidal composition in the form of pulverized powders for controlling weeds in paddy fields.

22. 988 parts of trioxane (1) was mixed thoroughly with 12 parts of allyl-2-methyl-4-chlorophenoxy acetate (hereinafter called MCP) to produce a herbicidal composition in the form of pulverized powders for controlling weeds in paddy fields.

23. 915 parts of trioxane (2) was mixed thoroughly with 70 parts of S-(4-chlorobenzyl)-N,N-diethyl-thiocarbamate and 15 parts of 2-methylthio-4,6-(bis ethylamino)-1,3,5-triazine to produce a herbicidal composition for controlling weeds in paddy and plowed fields.

24. 915 parts of trioxane (1) was mixed thoroughly with 85 parts of 3-amino-2,5-dichlorobenzoic acid to produce a herbicidal composition in the form of pulverized powders for killing weeds in soybean fields.

25. 910 parts of trioxane (2) was mixed thoroughly with 90 parts of 3-(3,4-dichlorophenyl)-1,1-dimethylurea to produce a herbicidal composition in the form of pulverized powder for killing weeds.

26. 915 parts of trioxane (2) was mixed thoroughly with 85 parts of 3,4-dichloropropionanilide to produce a herbicidal composition in the form of pulverized powder for killing weeds in paddy fields.

27. 910 parts of trioxane (1) was mixed thoroughly with 90 parts of S-(4-chlorobenzyl)-N,N-dimethyl-thiocarbamate to produce a herbicidal composition in the form of pulverized powder for killing weeds in paddy fields.

EXPERIMENTAL EXAMPLE 1

Paddy (Norin No. 8) was planted in three pots having a diameter of 12 cm. One gram of the malathion composition prepared in Example 1 was sprinkled on the paddy in the first pot. One gram of powder containing 97% of talc and 3% of malathion was sprinkled on the paddy in the second pot. No chemical was sprinkled on the one in the third pot for use as a control. On the day that the chemical was sprinkled, the fifth day and the eighth day thereafter, 20 larvae of *Nephotettix bipunctatus cincticeps* were released in each pot and the number of killed larvae was counted after 24 hours to determine the killing rate. The tests were carried out in a thermostatic chamber and were repeated three times. The results of the tests are as follows:

| When released after sprinkling | Killing Rate | | |
|---|---|---|---|
| | The same day | Fifth day after | Eight day after |
| Malathion + trioxane (1) | 100 | 90 | ⊖ |
| Malathion + talc | 100 | 61 | 5 |
| No chemical (control) | 0 | 0 | 0 |

These results show that the composition consisting of malathion and trioxane (1) remains effective for a longer period of time.

EXPERIMENTAL EXAMPLE 2

A mixture of trioxane (1), 30.0 grams, DDVP, 2.5 grams and Diazinon, 2.5 grams, said three chemicals having been thoroughly mixed with each other, were formed into a tablet measuring 60 mm in diameter and 12 mm in thickness. The single tablet was hung in a 1 $m^3$ box at the center thereof for determining the insect-killing effect of the tablet, putting 20 *Musca domestica* in the box in a closed state on every test-conducting day, the testing results being shown in the table below:

| Days of testing, starting with the setting of the test-tablet | Weight of the tablet (Unit:g) | Time required for entirely killing musca domestica (Unit:minute) |
|---|---|---|
| 1st day | 28.5 | 55 |
| 3rd day | 25.9 | 60 |
| 5th day | 24.3 | 60 |
| 10th day | 20.1 | 90 |
| 20th day | 12.5 | 180 |
| 30th day | 6.2 | 300 |

EXPERIMENTAL EXAMPLE 3

A mixture of trioxane (2), 20 grams, DDVP, 3 grams and Diazinon, 1 gram, the three constituents having been mixed thoroughly with each other, was formed into a tablet 60 mm in diameter and 8 mm thick. Said tablet was put in to test a method quite identical with Example 24, except that the testing period this time was longer by 10 days than in the case of Experimental Example 3, the results being shown in the table below:

| Days of testing, starting with the setting of the test-tablet | Weight of the tablet (Unit:g) | Time required for entirely killing the *Musca domestica* (Unit:minute) |
|---|---|---|
| 1st day | 22.0 | 60 |
| 3rd day | 20.1 | 60 |
| 5th day | 18.5 | 80 |
| 10th day | 15.1 | 100 |
| 20th day | 11.0 | 180 |
| 30th day | 7.5 | 330 |
| 40th day | 4.5 | 540 |

EXPERIMENTAL EXAMPLE 4

Paddy (Norin No. 8) was planted in six pots having a diameter of 12 cm. After it has put forth tillers, 1 gram of the powdery EDDP composition prepared in Example 18 was sprinkled on two pots. One gram of a powdery composition consisting of 97.5% of talc and 2.5% of EDDP was sprinkled on the other two pots. No chemicals were sprinkled on the remaining two pots for use as control. The paddy in one of each pair of the pots was inoculated on the day after sprinkling with *Piricularia oryzae* germs by spraying a suspension containing them. The paddy in the other of each pair of the pots was similarly inoculated on the fifth day after sprinkling. On the seventh day after inoculation, the area of the still-infected portions was measured and indicated in terms of percentage against the infected area of the control paddy.

| | Ratio to infected area of control paddy (in %) | |
|---|---|---|
| | A | B |
| EDDP + trioxane (1) | 0 | 8 |
| EDDP + talc | 0 | 47 |
| No chemicals used (control) | 100 | 100 |

A: When inoculated on the day after sprinkling
B: When inoculated on the fifth day after sprinkling

EXPERIMENTAL EXAMPLE 5

Four pots having a diameter of 10 cm were filled with soil of a paddy field to the depth of 10 cm, on which 50 grains of seeds of barnyard grass (*Echinochloa crusgalli*, Beauv., var. *edulis*, Honda) were sowed. A small amount of soil was put thereon and wetted with water. One gram of pulverized powder of the MCP composition prepared in Example 22 was sprinkled on the first pot. On the second pot was sprinkled, one gram of powder consisting of 12 parts of MCP and 988 parts of diatomaceous earth. On the third pot was sprinkled one gram of trioxane (1) powder only. No chemical was sprinkled on the fourth pot for use as a control. Twenty days later, the extent of germination of the grass in these four pots was checked to determine the effect of herbicidal compositions. After the first check, 50 grains of the same seed were sowed on the first, second and third pots. In the case of the third pot, the grass that had sprouted was removed before re-sowing. Twenty days after re-sowing, it was observed how much the germination was controlled. The effect of herbicidal compositions was evaluated against the control in the fourth pot.

| | At first check (in %) | At second check (in %) |
|---|---|---|
| 1st pot | 0 | 4 |
| 2nd pot | 0 | 78 |
| 3rd pot | 100 | — |
| 4th pot | 100 | 100 |

The above experiments show that trioxane (1) has no herbicidal effect, does no harm to plants, and remains effective for a longer period of time because of the small amount of decomposition of the herbicide compared to the conventional MCP powder.

The amount of the carrier in respect to the active agricultural ingredients is not critical. The mixing ratio is essentially the same as with conventional carrier-agricultural chemical combinations and depends on the type of material employed, the purpose of use, ease of use, the safety requirements in respect to men and animals, etc.

A typical agricultural composition in accordance with the present invention contains about 80%–99.8% of a carrier.

What is claimed is:

1. In a sublimable fungicidal composition in the form or rough grains, pulverized powders or tablets consisting essentially of an effective amount of at least one fungicide and a carrier therefor, said fungicide being intimately mixed with the carrier, the improvement wherein the carrier is triisopropyl-s-trioxane having a melting point of 62.5° C. or tritertiary butyl-s-trioxane having a melting point of 92.0° C.

2. A composition according to claim 1 wherein the carrier is triisopropyl-s-trioxane.

3. A composition according to claim 1 wherein the carrier is tritertiarybutyl-s-trioxane.

4. A composition according to claim 1, wherein the fungicide is O,O-diisopropyl-S-benzylthiophosphate.

5. A composition according to claim 1, wherein the fungicide is O-ethyl-S,S-diphenyldithiophosphate.

6. A composition according to claim 1, wherein the fungicide is O-butyl-S-ethyl-S-benzyl-phosphorodithioate.

7. A composition according to claim 1, wherein the fungicide is the hydrochloric salt of Kasugamycin.

8. A composition according to claim 1, wherein the carrier is present in an amount of 80–99.8%.